US00PP22764P3

(12) United States Plant Patent
Meilland

(10) Patent No.: US PP22,764 P3
(45) Date of Patent: Jun. 5, 2012

(54) HYBRID TEA ROSE PLANT NAMED 'MEIKOLYMA'

(50) Latin Name: *Rosa hybrida*
Varietal Denomination: Meikolyma

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/805,329

(22) Filed: Jul. 26, 2010

(65) Prior Publication Data

US 2012/0023628 P1 Jan. 26, 2012

(51) Int. Cl.
*A01H 5/00* (2006.01)

(52) U.S. Cl. ..... Plt./130

(58) Field of Classification Search ..... Plt./130, Plt./139, 140

See application file for complete search history.

*Primary Examiner* — June Hwu

(74) *Attorney, Agent, or Firm* — Buchanan Ingersoll & Rooney PC

(57) ABSTRACT

A new and distinct Hybrid Tea rose plant is provided that forms at mid-season abundantly and substantially continuously attractive bright red-purple blossoms. The medium-sized buds are globular-shaped. The growth habit is semi-erect, and the stems are extremely rigid. The vegetation is very strong and attractive very dense leathery glossy dark green foliage is formed. The plant is particularly well suited for providing attractive ornamentation in the landscape.

1 Drawing Sheet

Figures 1, 2, 3, 4, 5, 6, 7, 8, 9, 10, 11, 12, 13, 14, 15, 16:
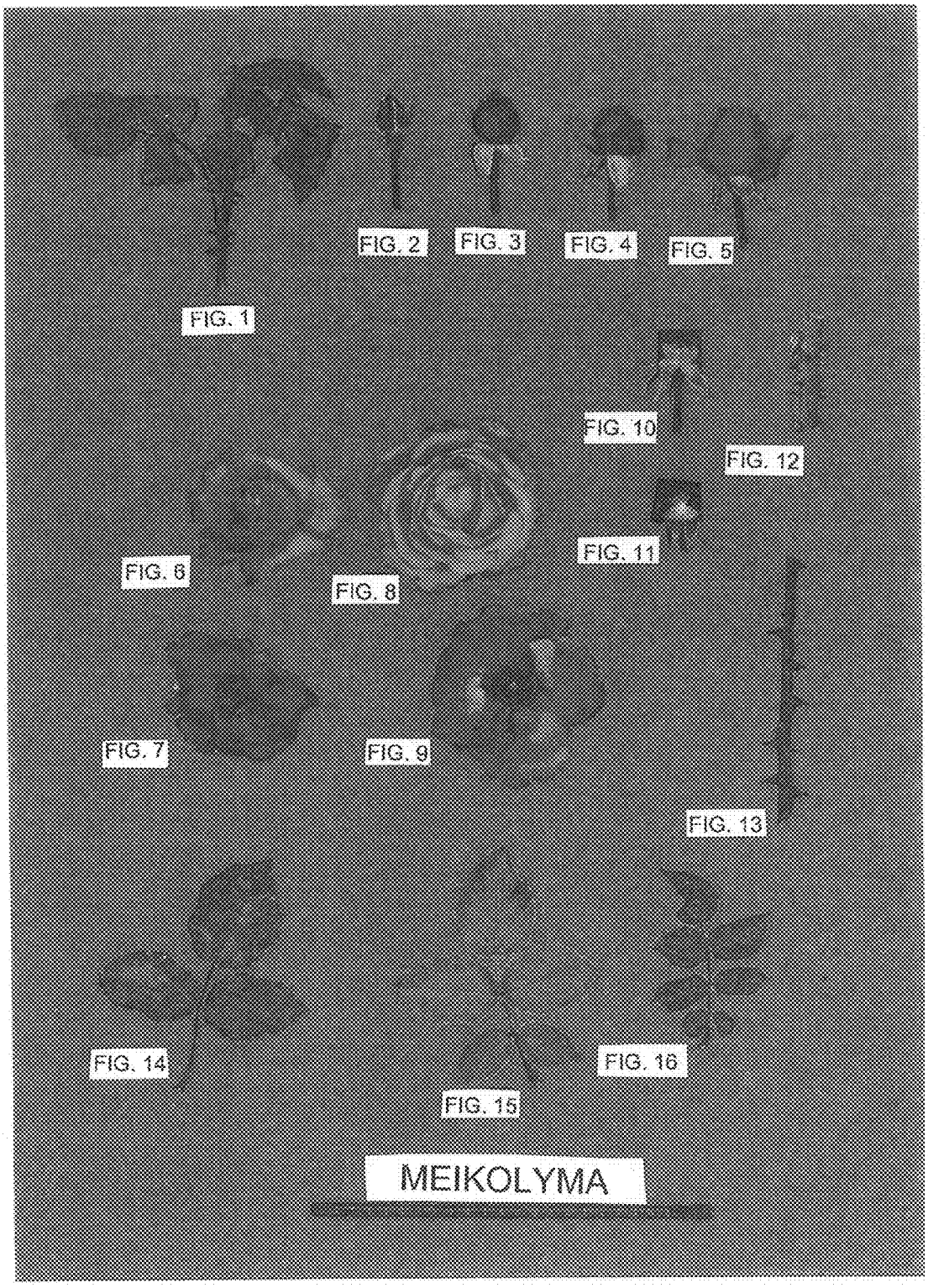

Botanical/commercial classification: *Rosa hybrida*/Hybrid Tea Rose Plant.

Varietal denomination: cv. Meikolyma.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the 'Macnon' variety (non-patented in the United States). The male parent (i.e., the pollen parent) was the product of the cross of the 'Meironsse' variety (U.S. Plant Pat. No. 8,496) and the 'Meipsilon' variety (non-patented in the United States).

The parentage of the new variety can be summarized as follows:

'Macnon'×('Meironsse'×'Meipsilon').

The seeds resulting from the above pollination were sown and small plants were obtained which were physically and biologically different from each other. Selective study resulted in the identification of a single plant of the new variety.

It was found that the new Hybrid Tea rose plant of the present invention:

(a) displays a semi-erect growth habit with strong vegetation and extremely rigid stems,
(b) forms medium-sized globular-shaped buds,
(c) forms at mid-season abundantly and substantially continuously attractive bright red-purple blossoms,
(d) displays attractive very dense leathery glossy dark green foliage, and
(e) is particularly well suited for providing attractive ornamentation in the landscape.

The blossoms tend to emit a very slight fragrance that is reminiscent of tea and cut grass.

The new variety well meets the needs of the horticultural industry and can be grown to advantage in the landscape.

The new variety can be readily distinguished from its ancestors. For instance, the blossom appearance is considerably different from that of the 'Macnon', 'Meironsse', and 'Meipsilon' varieties. More specifically, the 'Macnon' variety forms medium pink blossoms having a lesser number of petals, the 'Meironsse' variety forms blossoms which display an orange blend/copper coloration, and the 'Meipsilon' variety forms bicolored red and yellow blossoms.

The new variety also can be readily distinguished from the 'Meizeli' variety (U.S. Plant Pat. No. 8,391) and the 'Meizincaro' variety (U.S. Plant Pat. No. 11,660). The 'Meizeli' variety forms dissimilar pink blossoms having a substantially lesser number of petals. The 'Meizincaro' variety forms dissimilar Cardinal Red blossoms having a somewhat lesser number of petals.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meikolyma'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during October while budded on *Rosa laxa* understock and growing outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud at the opening of the sepals;

FIG. 3—illustrates a specimen of a floral bud wherein the sepals are fully open;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a main branch;

FIG. 13—illustrates a specimen of a flowering stem;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart)—1995 Edition or equivalent. The description is based on the observation of one-year-old plants during October which were budded on *Rosa laxa* understock and growing outdoors at Le Cannet des Maures, Var, France.

Class: Hybrid Tea.

Plant:

*Growth habit*.—Semi-erect.

Branches:

*Color*.—Young stems: near Yellow-Green Group 146A. Adult wood: near Yellow-Green Group 146B.

*Thorns*.—On young stems: Small prickles: Configuration: rather upright on both surfaces, and elongated on the upper surface with an ovate and short base. Quantity: approximately 2 on average on a stem length of 10 cm. Length: approximately 0.5 cm on average. Color: near Greyed-Orange Group 175B. Long prickles: Configuration: rather upright on both surfaces, and elongated on the upper surface with an obovate and long base. Quantity: approximately 15 on average on a stem length of 10 cm. Length: approximately 1 cm on average. Color: near Greyed-Orange Group 176B. On adult stems: Small prickles: Configuration: rather upright and very elongated on the upper surface and slightly concave on the under surface with an obovate and short base. Quantity: approximately 11 on average on a stem length of 10 cm. Length: approximately 0.4 cm on average. Color: near Greyed-Orange Group 175A. Long prickles: Configuration: rather upright and very elongated on the upper surface and slightly concave on the under surface with an obovate and long base. Quantity: approximately 16 on average on a stem length of 10 cm. Length: approximately 1 cm on average. Color near Greyed-Orange Group 177A.

Leaves:

*Stipules*.—Adnate, pectinate, rather broad, approximately 1.8 cm in length on average, approximately 0.6 cm in width on average, near Yellow-Green Group 146D on the upper surface, and near Yellow-Green Group 148A on the under surface.

*Petioles*.—Upper surface: near Yellow-Green Group 146B in coloration. Under surface: near Greyed-Red Group 181A in coloration. Length: approximately 4.7 cm on average for the terminal leaflet. Texture: glandular on the upper surface, and with small prickles on the under surface.

*Rachis*.—Upper surface: near Greyed-Purple Group 183A in coloration. Under surface: near Yellow-Green Group 148A in coloration. Texture: smooth.

*Leaves*.—Size: for a five-leaflet leaf approximately 15 to 17 cm in length on average and approximately 13 cm in width on average.

*Leaflets*.—Number 3, 5 (most often), and 7. Shape: generally oval with an acuminate tip and a rounded obtuse base. Size: the terminal leaflets commonly are approximately 7 cm in length on average and approximately 4.9 cm in width on average. Serration: small and single (as illustrated). Texture: physically firm and leathery. Color (young foliage): Upper surface: near Yellow-Green Group 146A. Under surface: near Greyed-Red Group 178A. Color (adult foliage): Upper surface: near Green Group 139A. Under surface: near Green Group 137C.

*Venation*.—Near Yellow-Green Group 146B on the upper surface and near Greyed-Red Group 181A on the under surface.

Inflorescence:

*Number of flowers*.—Commonly approximately 1 to 4 blossoms per stem.

*Peduncle*.—Smooth, approximately 6 to 7 cm in length on average, approximately 0.4 cm in diameter on average, and near Greyed-Purple Group 183A in coloration.

*Sepals*.—Upper surface: tomentose and near Greyed-Orange Group 177C in coloration. Under surface: smooth and near Yellow-Green Group 146C in coloration. Shape: longish and narrow, and somewhat upright at the base. Size: approximately 2.9 cm in length on average, and approximately 1 cm in width at the widest point on average.

*Buds*.—Shape: substantially globular. Size: medium. Length: approximately 2 to 2.5 cm on average. Width: approximately 2.5 cm at the widest point on average. Color as calyx breaks: Upper surface: near Red-Purple Group 68B. Under surface: near Red-Purple Group 58B.

*Flower*.—Shape: cup-shaped. Diameter: approximately 13 cm on average. Height: approximately 6 cm when open. Color (in the course of opening): Upper surface: near Red-Purple Group 62A. Under surface: near Red-Purple Group 58B. Color (open flower): Upper side: near Red-Purple Group 62C. Under side: near Red-Purple Group 62A. Fragrance: very slight and resembles that of tea and cut grass. Petal number:

approximately 67 to 70 on average under normal growing conditions. Petal shape: with a substantially rounded tip and a cuneiform base. Petal texture: leathery and somewhat firm. Petal length: approximately 4.6 cm on average. Petal width: approximately 4.2 cm on average. Petal arrangement: imbricated, and without petaloids. Petal drop: good with the petals commonly detaching cleanly before drying. Stamen number: approximately 142 on average. Anthers: regularly arranged in a whorl around the styles, approximately 0.3 cm in size on average, and near Yellow-Orange Group 15A in coloration. Filaments: approximately 0.5 cm in length on average, and near Yellow Group 9A in coloration. Pollen: yellow-orange in coloration. Pistils: approximately 108 on average. Stigmas: approximately 0.2 cm in size on average, and near Red Group 43A in coloration. Styles: approximately 0.9 cm in length on average, and near Yellow Group 2D in coloration. Receptacle: smooth, pitcher-shaped in longitudinal section, approximately 1.9 cm in length on average, approximately 1.2 cm in width on average at the widest point, and near Yellow-Green Group 146B in coloration. Hips: generally smooth in texture, approximately 2.5 cm in size, and near Orange Group 25C in coloration.

Development:

*Vegetation*.—Strong.

*Blooming*.—Mid-season, very abundant and substantially continuous.

*Tolerance to diseases*.—Good, with no particular susceptibility to common diseases having been encountered during observations to date. Lastingness: approximately 7 to 12 days on the plant under typical growing conditions with no lastingness evaluation having been conducted when present in a vase since variety is primarily intended to be observed in the garden.

I claim:

1. A new and distinct Hybrid Tea rose plant characterized by the following characteristics:

(a) displays a semi-erect growth habit with strong vegetation and extremely rigid stems, (b) forms medium-sized globular-shaped buds, (c) forms at mid-season abundantly and substantially continuously attractive bright red-purple blossoms, (d) displays attractive very dense leathery glossy dark green foliage, and (e) is particularly well suited for providing attractive ornamentation in the landscape;

substantially as shown and described.

* * * * *

MEIKOLYMA